United States Patent [19]

Strojny

[11] 3,963,759

[45] June 15, 1976

[54] OXIDATION OF MESITYL OXIDE TO CITRACONIC ANHYDRIDE

[75] Inventor: Edwin J. Strojny, Midland, Mich.

[73] Assignee: The Dow Chemical Company, Midland, Mich.

[22] Filed: June 7, 1973

[21] Appl. No.: 367,912

[52] U.S. Cl. ............... 260/346.8 A; 252/461; 252/472; 252/437; 252/443; 252/467
[51] Int. Cl.$^2$ .................................. C07D 307/56
[58] Field of Search ............... 260/346.8 A, 346.8

[56] References Cited
UNITED STATES PATENTS 2,443,818   6/1948   Elce et al. .................. 260/526 N
3,228,966   1/1966   Adams ....................... 260/346.1

*Primary Examiner*—Harry I. Moatz
*Attorney, Agent, or Firm*—Chessie E. Rehberg; Ralph M. Mellom

[57] ABSTRACT

Citraconic anhydride is made by the vanadium-catalyzed gas-phase air oxidation of mesityl oxide at about 200-500°C. and atmospheric pressure with a contact time of less than 1 second. Preferred catalysts are vanadium oxide and vanadate salts. Preferred $O_2$/mesityl oxide molar ratios are about 10:1 to 100:1.

8 Claims, No Drawings

OXIDATION OF MESITYL OXIDE TO CITRACONIC ANHYDRIDE

BACKGROUND OF THE INVENTION

Mesityl oxide has been oxidized with air over various catalysts, including $V_2O_5$, with molar ratios of $O_2$ to mesityl oxide of 1:1 to 2:1 and temperatures of 418–608°C. to produce dimethylfuran (U.S. Pat. No. 3,228,966). If any citraconic anhydride was produced it apparently was not recognized.

Mesityl oxide has been oxidized in the liquid phase with air over a cobalt catalyst at 70°–120°C. Vanadium salts were said to be useful as a replacement for the cobalt catalyst. The only identified product was α-methyl-β-acetylacrylic acid (U.S. Pat. No. 2,443,818).

Citraconic anhydride has been made by the acetylation and pyrolysis of citramalic acid (Kunichika et al., Kyoto University Institute for Chemical Research Bulletin, 44, No. 3, pp. 221–225 (1966)).

SUMMARY OF THE INVENTION

Citraconic anhydride is made by oxidizing mesityl oxide with oxygen (air) in the vapor phase over a vanadium catalyst. The molar ratio of $O_2$ to mesityl oxide is at least about 10:1 and may be 100:1 or more.

DETAILED DESCRIPTION OF THE INVENTION

The process of the invention is conveniently operated at atmospheric pressure, though higher or lower pressures can be used if desired.

The catalyst is a vanadium-containing compound, such as vanadium oxide, vanadate salts and vanadyl salts. Other catalytic elements may be used in combination with vanadium. Thus, vanadium-molybdenum oxides, vanadium-tungsten oxides, vanadium-cobalt oxides and the like are useful. Useful oxide catalysts are provided by the surface oxidation of elemental vanadium or of vanadium alloys with iron, cobalt, tungsten or other heavy metals. If desired, the catalyst may be deposited on a suitable catalyst support. Suitable supports include alumina, silica, pumice, silicon carbide and the like.

The catalyst, in appropriate physical form (granules, beads, powder, etc.), may be used as a fixed bed or as a fluidized bed.

While pure oxygen can be used as the oxidizing agent in the process, air is preferred as a practical matter. The molar ratio of $O_2$ to mesityl oxide should be at least about 10:1 and may be as high as 100:1 or more, though little advantage has been found for ratios above about 80:1. Even though the yields are higher at such high ratios, the excessive dilution of the product increases the cost of operating the process. Since the calculated lower explosive limit of the reaction mixture (with air) is about 15:1, it is preferred that the ratio be above this value in order to minimize the danger of explosion, though operation of pyrolytic processes within the explosive limits is known, especially when fluidized catalyst beds are used.

The reaction temperature of the process can be varied widely, the optimum depending on the particular catalyst used, whether the catalyst bed is fixed or fluidized, the oxygen ratio and the space velocity of the reactants. Once the other parameters are fixed, it is a simple matter to vary the temperature to find the optimum value. Likewise, the other process parameters can be optimized by a few routine experiments.

The vanadium oxide catalysts usually show little activity below about 350°C. In a fixed bed they function best at about 375°–400°while above about 400°the yields diminish. In a fluidized bed and/or when the catalyst is diluted, somewhat higher temperatures are suitable. Those catalysts containing tin, e.g., tin vanadate, are most efficient at much lower temperatures — about 215°–240°C., while those containing tungsten or molybdenum work best at somewhat higher temperatures, e.g., 480°–500°C.

The reaction time may be varied from the shortest time that results in a significant amount of reaction to the time required for essentially complete conversion of the mesityl oxide. These times, of course, will vary widely with temperatures, reactant ratios, catalysts, etc. Reaction times are usually expressed either as "contact time," calculated on the volume of gaseous feed mixture at reaction temperature or as "gaseous hourly space velocity" (GHSV), based on the volume of gaseous feed, calculated at 27°C. and 1 atmosphere pressure, and the volume of the static catalyst bed, assuming zero volume for the catalyst itself, i.e., assuming 100% free space in the catalyst bed. Obviously, the contact time varies inversely with the GHSV.

In carrying out the process, the mesityl oxide is vaporized, mixed with the desired proportion of air or other oxygen-containing gas, brought up to reaction temperature, either by use of a preheater or by passing the mixture directly into the reactor containing the catalyst, and contacted with the catalyst at the chosen temperature. The reaction mixture is then cooled and the products condensed. Because of the large volume of noncondensable gas, an efficient low-temperature condenser is needed to minimize losses of product. The collected product is analyzed and found to consist essentially of citraconic anhydride containing small amounts of acetic acid and/or maleic anhydride. The acetic acid is easily removed by distillation. While the maleic anhydride can also be separated, for many purposes its presence is not objectionable, e.g., in making unsaturated polyesters.

SPECIFIC EMBODIMENTS OF THE INVENTION

The following examples illustrate the practice of the invention.

EXAMPLE 1

Vanadium pellets of 14–20 mesh size were oxidized in air at 550°C. for 24 hours. Ten cc. of this catalyst was packed in a 15 mm. o.d. U-shaped Vycor glass tube. This reactor was immersed in a salt bath held at 381°–384°C. while a mixture of 0.6 g./min. of vaporized mesityl oxide and 1.56 l. (25°C.)/min. of air was passed through it (GHSV = 9500; $O_2$/mesityl oxide ratio, 20:1). The effluent was passed through successive condensers cooled with tap water, ice and Dry Ice. The combined condensate was analyzed by GLC and found to contain the following:

| | |
|---|---|
| Mesityl oxide | 0 |
| Citraconic anhydride | 30.7% |
| Maleic anhydride | 4.1 |
| Acetic acid | 3.9 |

(All percentages are by weight, based on the mesityl oxide fed).

EXAMPLES 2-18

In experiments generally similar to that of Example 1, other catalysts, feed rates and oxygen ratios were used, as well as different sizes of reactors. The results are summarized in the following table. In every experiment, the mesityl oxide was completely converted.

TABLE I

| Ex. No. | Catalyst | Temp., °C. | GHSV | Oxygen Ratio | Reactor Cross-Section, Cm.$^2$ | Acetic Acid | Products, Wt. %$^a$ Maleic Anhydride | Citraconic Anhydride |
|---|---|---|---|---|---|---|---|---|
| 2 | Oxidized Fe-V Alloy | 390 | 9450 | 21.1 | 1.0 | 4.6 | 6.1 | 30.3 |
| 3 | Oxidized V on V surface | 388 | 8600 | 20.5 | 1.0 | 12.8 | 4.2 | 31.0 |
| 4 | 10% $V_2O_5$ on $Al_2O_3$ Harshaw VO501 | 371 | 9450 | 21.0 | 1.0 | 2.7 | 3.2 | 19.5 |
| 5 | 5% $V_2O_5$-5% $MoO_3$ on $Al_2O_3$ Harshaw V1001E | 400 | 11030 | 21.2 | 1.0 | 7.8 | 4.3 | 14.7 |
| 6 | 0.5% $V_2O_5$ on $Al_2O_3$ | 438 | 8000 | 21.0 | 1.0 | 6.2 | 5.6 | 21.5 |
| 7 | Fused $V_2O_5$ | 378 | 8020 | 40.8 | 1.0 | 10.5 | 3.3 | 38.6 |
| 8 | Fused $V_2O_5$ | 381 | 8000 | 40.0 | 26.4 | 15.2 | 3.7 | 40.6 |
| 9 | Fused $V_2O_5$ | 431 | 24000 | 78.0 | 3.3$^b$ | 7.1 | 2.0 | 39.0 |
| 10 | Fused $V_2O_5$ | 430 | 38000 | 84.0 | 3.3$^b$ | 8.5 | 2.5 | 41.7 |
| 11 | Fused $V_2O_5$ Diluted 1:6 with SiC | 372 | 4000 | 42.7 | 0.5 | 34.8 | 2.4 | 26.2 |
| 12 | Fused $V_2O_5$ + 1000 ppm. Cu | 381 | 8000 | 50.0 | 1.0 | 9.6 | 3.0 | 33.2 |
| 13 | 18.6% $V_2O_5$, 20.7% $WO_3$, 12.9% $P_2O_5$ on $SiO_2$ (Celite)$^c$ | 399 | 8000 | 40.0 | 1.0 | 11.4 | 3.6 | 32.1 |
| 14 | $CoO_3$-$V_2O_5$ (1:10) on Pumice | 362 | 8000 | 40.0 | 1.0 | 7.1 | .01 | 19.1 |
| 15 | 4.2% $MoO_3$, 23.8% $V_2O_5$ on Pumice | 374 | 9000 | 80.0 | 1.0 | 6.0 | 3.6 | 21.2 |
| 16 | Tin Vanadate | 220 | 7940 | 19.9 | 1.0 | 5.1 | 2.5 | 22.3 |
| 17 | Tin Vanadate | 299 | 16000 | 40.0 | 3.3$^b$ | 15.0 | 2.4 | 23.9 |
| 18 | 0.18% $V_2O_5$, 28.8% $TiO_2$, 0.17% $PO_4^{-3}$ on SiC$^d$ | 375 | 16000 | 32.0 | 3.3 | 12.2 | 3.0 | 36.4 |

$^a$Based on mesityl oxide fed
$^b$Fluidized catalyst bed
$^c$Catalyst made as described in British Pat. No. 920,853
$^d$Catalyst made as described in U.S. Pat. No. 3,684,741

I claim:

1. The process of making citraconic anhydride comprising contacting a gaseous mixture of mesityl oxide and air or oxygen with a catalyst comprising vanadium oxide, a vanadate salt or a vanadyl salt at reaction temperature, said gaseous mixture containing at least about 10 moles of oxygen per mole of mesityl oxide.

2. The process of claim 1 wherein at least 15 moles of oxygen are present per mole of mesityl oxide.

3. The process of claim 1 wherein the catalyst comprises vanadium oxide.

4. The process of claim 1 wherein the catalyst is in the form of a fluidized bed of solid particles.

5. The process of claim 1 wherein the temperature is about 200°–500°C.

6. The process of claim 1 wherein the gaseous hourly space velocity as defined herein is about 8000–40,000.

7. The process of claim 1 wherein the catalyst comprises tin vanadate.

8. The process of claim 1 wherein the catalyst consists essentially of vanadium oxide or tin vanadate.

* * * * *